US009125881B2

(12) United States Patent
Henderson (10) Patent No.: US 9,125,881 B2
(45) Date of Patent: Sep. 8, 2015

(54) MONOGLYCERIDE OF ACETOACETATE AND DERIVATIVES FOR THE TREATMENT OF NEUROLOGICAL DISORDERS

(75) Inventor: Samuel T. Henderson, Golden, CO (US)

(73) Assignee: Accera, Inc., Broomfield, CO (US)

( * ) Notice: Subject to any disclaimer, the term of this patent is extended or adjusted under 35 U.S.C. 154(b) by 163 days.

(21) Appl. No.: 13/054,053

(22) PCT Filed: Jul. 2, 2009

(86) PCT No.: PCT/US2009/049609
§ 371 (c)(1),
(2), (4) Date: Jan. 13, 2011

(87) PCT Pub. No.: WO2010/003114
PCT Pub. Date: Jan. 7, 2010

(65) Prior Publication Data
US 2011/0178032 A1    Jul. 21, 2011

Related U.S. Application Data

(60) Provisional application No. 61/078,214, filed on Jul. 3, 2008.

(51) Int. Cl.

| | |
|---|---|
| *A61K 31/22* | (2006.01) |
| *A61K 31/7004* | (2006.01) |
| *A61P 25/28* | (2006.01) |
| *A23L 1/30* | (2006.01) |
| *A23L 2/52* | (2006.01) |
| *A61K 9/00* | (2006.01) |
| *A61K 9/10* | (2006.01) |
| *A61K 9/20* | (2006.01) |
| *A61K 9/48* | (2006.01) |
| *A61K 31/047* | (2006.01) |

(52) U.S. Cl.
CPC . *A61K 31/22* (2013.01); *A23L 1/30* (2013.01); *A23L 2/52* (2013.01); *A61K 9/0019* (2013.01); *A61K 9/0095* (2013.01); *A61K 9/10* (2013.01); *A61K 9/2054* (2013.01); *A61K 9/4866* (2013.01); *A61K 31/047* (2013.01); *A61K 31/7004* (2013.01)

(58) Field of Classification Search
CPC .......................... A61K 31/7004; A61K 31/20
See application file for complete search history.

(56) References Cited

U.S. PATENT DOCUMENTS

| | | |
|---|---|---|
| 2,766,145 A | 10/1956 | O'Brien |
| 2,766,146 A | 10/1956 | Gilbert |
| 3,053,677 A | 9/1962 | Touey |
| 4,346,107 A | 8/1982 | Cavazza et al. |
| 4,407,821 A | 10/1983 | Mendy |
| 4,528,197 A | 7/1985 | Blackburn |
| 4,551,523 A | 11/1985 | Elam |
| 4,687,782 A | 8/1987 | Brantman |
| 4,847,296 A | 7/1989 | Babayan et al. |
| 5,093,044 A | 3/1992 | Wretlind |
| 5,118,670 A | 6/1992 | Wurtman et al. |
| 5,126,373 A | 6/1992 | Brunengraber et al. |
| 5,175,190 A | 12/1992 | Burton et al. |
| 5,276,059 A | 1/1994 | Caughey et al. |
| 5,308,832 A | 5/1994 | Garleb et al. |
| 5,385,915 A | 1/1995 | Buxbaum et al. |
| 5,391,375 A | 2/1995 | Hille et al. |
| 5,420,335 A | 5/1995 | Birkhahn et al. |
| 5,494,794 A | 2/1996 | Wallace |
| 5,504,072 A | 4/1996 | Schmidl et al. |
| 5,508,167 A | 4/1996 | Roses et al. |
| 5,538,983 A | 7/1996 | Buxbaum et al. |
| 5,607,967 A | 3/1997 | Friedman et al. |
| 5,614,560 A | 3/1997 | Lipton |
| 5,650,148 A | 7/1997 | Gage et al. |
| 5,691,325 A | 11/1997 | Sandyk |
| 5,693,850 A | 12/1997 | Birkhahn et al. |
| 5,716,828 A | 2/1998 | Roses et al. |
| 5,766,621 A | 6/1998 | Trimbo et al. |
| 5,817,626 A | 10/1998 | Findeis et al. |
| 5,854,204 A | 12/1998 | Findeis et al. |
| 5,854,215 A | 12/1998 | Findeis et al. |
| 5,925,684 A | 7/1999 | Schweikert et al. |
| 5,935,781 A | 8/1999 | Poirier |

(Continued)

FOREIGN PATENT DOCUMENTS

| | | |
|---|---|---|
| CN | 1316902 | 10/2001 |
| CN | 1681941 | 10/2005 |

(Continued)

OTHER PUBLICATIONS

Hiroyuki et al., machine translation of JP 06-287138, obtained Apr. 6, 2010, 9 pages.*
Ogden, C. L. et al., Centers for Disease Control and Prevention, Advance Data From Vital and Health Statistics, "Mean Body Weight, Height, and Body Mass Index, United States 1960-2002", Oct. 2004, No. 347, 18 pages.*
Poirier, J. et al., Proc. Natl. Acad. Sci., "Apolipoprotein E4 Allele as a Predictor of Cholinergic Deficits and Treatment Outcome in Alzheimer Disease", 1995, vol. 92, pp. 12260-12264.*
Birkhahn et al., (May 1994) Parenteral Monoacetoacetin and Liver Regeneration Interaction After Partial 6 Hepatectomy in the Rat, Journal of Parenteral and Enteral Nutrition, 18(3):219-224, abstract.
Ko et al. (Mar. 1999) "Bile Salts: Metabolic patholigic, and therapeutic considerations," Gastroenterology 7 Clinics, 28(1):108-116.
International Search Report and Written Opinion prepared by the U.S. Patent and Trademark Office as International Searching Authority for PCT International Patent Application No. PCT/US2009/049609, mailed Sep. 16, 2009, 11 pages.

(Continued)

*Primary Examiner* — Shaojia Anna Jiang
*Assistant Examiner* — Bahar Craigo
(74) *Attorney, Agent, or Firm* — Swanson & Bratschun, L.L.C.

(57) ABSTRACT

This invention relates to methods of using the monoglyceride of acetoacetate and metabolic precursors for the treatment, prevention, inhibition or alleviation of neurological diseases associated with neuronal hypometabolism, such as Alzheimer's disease, Parkinson's disease, Friedreich's Ataxia (FRDA), GLUT1-deficient Epilepsy, Leprechaunism and Rabson-Mendenhall Syndrome, Coronary Arterial Bypass Graft (CABG) dementia, anesthesia induced memory loss, age associated memory impairment (AAMI), Traumatic Brain Injury (TBI), Huntington's disease and many others.

5 Claims, 3 Drawing Sheets

(56) References Cited

U.S. PATENT DOCUMENTS

| | | |
|---|---|---|
| 5,936,078 A | 8/1999 | Kuga et al. |
| 5,980,939 A | 11/1999 | Kim et al. |
| 6,027,896 A | 2/2000 | Roses et al. |
| 6,136,862 A | 10/2000 | Hiraide et al. |
| 6,159,942 A | 12/2000 | Cyr et al. |
| 6,207,856 B1 | 3/2001 | Veech |
| 6,232,345 B1 | 5/2001 | Hiraide et al. |
| 6,316,038 B1 | 11/2001 | Veech |
| 6,323,237 B1 | 11/2001 | Veech |
| 6,380,244 B2 | 4/2002 | Martin |
| 6,395,306 B1 | 5/2002 | Cui et al. |
| 6,835,750 B1 | 12/2004 | Henderson |
| 6,884,454 B2 | 4/2005 | Pimentel |
| 7,001,736 B1 | 2/2006 | Poirier |
| 7,049,078 B2 | 5/2006 | Poirier |
| 7,087,649 B2 | 8/2006 | Barth et al. |
| 7,622,470 B2 | 11/2009 | O'Connor et al. |
| 7,939,530 B2 | 5/2011 | O'Connor et al. |
| 8,124,589 B2 | 2/2012 | Henderson |
| 8,445,535 B1 | 5/2013 | Henderson |
| 8,748,400 B2 | 6/2014 | Henderson |
| 2001/0041736 A1 | 11/2001 | Veech |
| 2002/0006959 A1 | 1/2002 | Henderson |
| 2002/0103139 A1 | 8/2002 | Weisspapir et al. |
| 2003/0059824 A1 | 3/2003 | Henderson |
| 2004/0052926 A1 | 3/2004 | Apfelbaum |
| 2004/0058873 A1 | 3/2004 | Esmond et al. |
| 2004/0060077 A1 | 3/2004 | Esmond |
| 2005/0009031 A1 | 1/2005 | Becker |
| 2005/0013884 A1 | 1/2005 | Rennels |
| 2005/0031651 A1 | 2/2005 | Gervais |
| 2005/0043242 A1 | 2/2005 | Esmond |
| 2006/0122270 A1 | 6/2006 | Henderson |
| 2006/0134240 A1 | 6/2006 | Miljkovic |
| 2006/0189545 A1 | 8/2006 | Henderson |
| 2006/0280721 A1 | 12/2006 | Veech et al. |
| 2007/0066527 A1 | 3/2007 | Tezapsidis |
| 2007/0179197 A1 | 8/2007 | Henderson |
| 2008/0287372 A1 | 11/2008 | Henderson |
| 2011/0243885 A1 | 10/2011 | Henderson |
| 2013/0005693 A1 | 1/2013 | Henderson |
| 2014/0256808 A1 | 9/2014 | Henderson |

FOREIGN PATENT DOCUMENTS

| | | | |
|---|---|---|---|
| CN | 1756554 | 4/2006 | |
| EP | 0519727 | 12/1992 | |
| EP | 0443996 | 6/1994 | |
| EP | 0676205 | 10/1995 | |
| EP | 0808626 | 11/1997 | |
| EP | 1419768 A1 | 5/2004 | |
| EP | 1813630 A2 | 8/2007 | |
| GB | 2368011 | 4/2002 | |
| JP | 05-097785 | 4/1993 | |
| JP | 06-287138 A * | 10/1994 | ............. A61K 31/23 |
| JP | 2006-287138 | 11/1994 | |
| JP | 2003-48831 A | 2/2003 | |
| JP | 2003-531857 | 10/2003 | |
| JP | 3486778 | 1/2004 | |
| JP | 2006-519843 | 8/2006 | |
| JP | 2007-217686 | 8/2007 | |
| JP | 2008-104359 | 5/2008 | |
| JP | 2009-524587 A | 7/2009 | |
| WO | WO 91/15963 | 10/1991 | |
| WO | WO 95/09146 | 4/1995 | |
| WO | WO 96/14063 | 5/1996 | |
| WO | WO 98/41200 | 9/1998 | |
| WO | WO 98/41201 | 9/1998 | |
| WO | WO 99/33853 | 7/1999 | |
| WO | WO 99/51097 | 10/1999 | |
| WO | WO 00/04895 | 2/2000 | |
| WO | WO 00/15216 | 3/2000 | |
| WO | WO 00/61079 | 10/2000 | |
| WO | WO 01/82928 | 11/2001 | |
| WO | WO 02/18400 | 3/2002 | |
| WO | WO 02/053121 | 7/2002 | |
| WO | WO 03/045429 | 6/2003 | |
| WO | WO 2004/077938 | 9/2004 | |
| WO | WO 2004/108740 | 12/2004 | |
| WO | WO 2005/074970 | 8/2005 | |
| WO | WO 2007/070701 | 6/2007 | |
| WO | WO 2007/115282 | 10/2007 | |
| WO | WO 2008/005818 | 1/2008 | |
| WO | WO 2008/005818 A1 * | 1/2008 | ............. A61K 31/22 |

OTHER PUBLICATIONS

Article World "human weight" also available at http://www.articleworld.org/index.php?title=Human_weight&printable=yes; last viewed Apr. 6, 2010.

Babayan (1987) Lipids 22(6):417-420 "Speciality Lipids and Their Biofunctionality".

Bach et al. (1982) Amer. J. Clinic. Nutr. 36:950-962 "Medium-chain triglycerides: an update".

Bach (1996) J. Lipid Res. 37:708 "The usefulness of dietary medium-chain triglycerides in body weight control: fact or fancy?"

Beckman and Ames (1998) Physiological Reviews 78(2):547-581 "The Free Radical Theory of Aging Matures".

Beffert et al. (1998) Brain Research Reviews 27:119-142 "The neurobiology of apolipoproteins and their receptors in the CNS and Alzheimer's disease".

Blass and Zemcov (1984) Neurochemical Pathology 2:103-114 "Alzheimer's Disease: A Metabolic Systems Degeneration?"

Blass (2001) Journal of Neuroscience Research 66:851-856 "Brain Metabolism and Brain Disease: Metabolic Deficiency the Proximate Cause of Alzheimer Dementia?"

Blazquez et al. (1998) J. N eurochem. 71: 1597-1606 "Role of carnitine palmitoyltransferase I in the control of ketogenesis in primary cultures of rat astrocytes".

Blazquez et al. (1999) J. Neurochemistry 72:1759-1768 "The Stimulation of Ketogenesis by Cannabinoids in Cultured Astrocytes Defines Carnitine Palitoyltransferase I as a New Ceramide-Activated Enzyme".

Blazquez et al. (1999) Journal of Neurochemistry 73:1674-1682 "The AMP-Activated Protein Kinase Is Involved in the Regulation of Ketone Body Production by Astrocytes".

Bröer et al. (1997) The Journal of Biological Chemistry 272(48):30096-30102 "Comparison of Lactate Transport in Astroglial Cells and Monocarboxylate Transporter 1 (MCT 1) Expressing *Xenopus laevis* Oocytes".

Brosnan and Brosnan (2006) Journal of Nutrition 136(1):207S-211S "Branched-Chain Amino Acids: Metabolism, Physiological Function, and Application".

Bruno et al. (1995) Alzheimer Disease and Associated Disorders 3:128-131 "Acetyl-L-Carnitine in Alzheimer disease: a short-term study on CSF neurotransmitters and neuropeptides".

Bullock (2002) British Journal of Psychiatry 180:135-139 "New drugs for Alzheimer's disease and other dementias".

Corbo and Scacchi (1999) Ann. Hum. Genet. 63:301-310 "Apolipoprotein E (APOE) allele distribution in the world. Is APOE*4 a 'thrifty' allele?"

Cox et al. (1998) The Journal of Pediatrics 133(2):247-253 "Reversal of severe hypertrophic cardiomyopathy and excellent neuropsychologic outcome in very-long-chain acyl-coenzyme A dehydrogenase deficiency".

Craft et al. (1996) Neurobiology of Aging 17(1):123-130 "Memory Improvement Following Induced Hyperinsulinemia in Alzheimer's Disease".

Crook et al. (1986) Developmental Neuropsychology 2(4):261-276 "Age-associated memory impairment: Proposed diagnostic criteria and measures of clinical change—report of a national institute of mental health work group".

Cruz et al. (2001) The Journal of Biological Chemistry 276(15):12162-12168 "Glucose and Insulin Stimulate Heparin-releaseable Lipoprotein Lipase Activity in Mouse Islets and INS-1 Cells".

Davis and Chisholm (1999) Nature 400:810 "Kansas makes a monkey of itself".

(56) References Cited

OTHER PUBLICATIONS

DeCarli (2003) The Lancet Neurology 2:15-21 "Mild cognitive impairment: prevalence, prognosis, aetiology, and treatment".
de Vries et al. (1997) Biochemistry 36:5285-5292 "Functional Characterization of Mitochondrial Carnitine Palmitoyltransferases I and II Expressed in the Yeast *Pichia pastoris*".
Dewachter et al. (2002) The Journal of Neuroscience 22(9):3445-3453 "Neuronal Deficiency of Presenilin 1 Inhibits Amyloid Plaque Formation and Corrects Hippocampal Long-Term Potentiation But Not a Cognitive Defect of Amyloid Precursor Protein [V717I] Transgenic Mice".
Dialog Results (Sep. 22, 2003) Agent for Prevention and/or therapeutics of Alzheimer's diseasecontg. Triglyceride of 8-10 carbon fatty acids as active ingredient, Translation of Publication No. 06-287138.
Dias (1990) Metabolism 39(9):887 "Effects of Medium-Chain Triglyceride Feeding on Energy Balance in Adult Human".
Edmond (1992) Can. J. Physiol. Pharmacol. 70:S118-S129 "Energy Metabolism in Developing Brain Cells".
Ettmayer et al. (2004) Journal of Medicinal Chemistry 47(10):2393-2404 "Lessons Learned from Marketed and Investigational Prodrugs".
Evans et al. (1989) JAMA 262(18):2551-2556 "Prevalence of Alzheimer's Disease in a Community Population of Older Persons: Higher than Previously Reported".
Extended European Search Report for EP 07797196.8, dated Aug. 24, 2009, 5 pages.
Finch and Cohen (1997) Experimental Neurology 143:82-102 "Aging, Metabolism, and Alzheimer Disease: Review and Hypotheses".
Fratiglioni et al. (1991) Neurology 41:1886-1892 "Prevalence of Alzheimer's disease and other dementias in an elderly urban population: Relationship with age, sex, and education".
Freeman et al. (2006) Epilepsy Research 68:145-180 "The ketogenic diet: From molecular mechanisms to clinical effects".
Frölich et al. (1998) J Neural Transm 105:423-438 "Brain insulin and insulin receptors in aging and sporadic Alzheimer's disease".
Gelman et al. (1999) Cellular and Molecular Life Sciences 55:932-943 "An update on the mechanisms of action of the peroxisome proliferator-activated receptors (PPARs) and their roles in inflammation and cancer".
George et al. (2004) Neurobiology of Disease 16:124-132 "APP intracellular domain is increased and soluble Aβ is reduced with diet-induced hypercholesterolemia in a transgenic mouse model of Alzheimer disease".
Goodman and Gilman (1996) The Pharmacological Basis of Therapeutics, 8th Edition, McGraw-Hill, Table of Contents.
Grant (1997) Alzheimer's Disease Review 2:42-55 "Dietary Links to Alzheimer's Disease".
Greenberg et al. (2000) Arch. Neurol. 57:94-99 "Donepezil Therapy in Clinical Practice".
Gregg et al. (1986) The Journal of Clinical Investigation, Inc. 78:815-821 "Abnormal In Vivo Metabolism of Apolipoprotein E4 in Humans".
Guillot et al. (1993) Brit. J. of Nutri. 69(2):431-42 "Intestinal absorption and liver uptake of medium-chain fatty acids in non-anaesthetized pigs".
Guzmán and Blazquez (2001) Trends in Endocrinology & Metabolism 12(4):169-173 "Is there an astrocyte-neuron ketone body shuttle?"
Haan and Wallace (2004) Annu. Rev. Public Health 25:1-24 "Can Dementia Be Prevented? Brain Aging in a Population-Based Context".
Halestrap and Price (1999) Biochem. J. 343:281-299 "The proton-linked monocarboxylate trasporter (MCT) family: structure, function and regulation".
Hall et al. (1998) Australian and New Zealand Journal of Psychiatry 32:698-706 "Risk factors and Alzheimer's disease: a comparative study of two communities".
Hamosh (1990) Lingual and Gastric Lipases: Their Role in Fat Digestion, CRC Press, Boca Raton, FL, Table of Contents and relevant pages.
Hanlon and Rubinsztein (1995) Atherosclerosis 112:85-90 "Arginine residues at codons 112 and 158 in the apolipoprotein E gene correspond to the ancestral state in humans".
Hänninen (1996) Neurologian klinikan julkaisusarja 39:1-34 "Age-Associated Memory Impairment".
Hasselbalch et al. (1996) The American Physiological Society, Cerebral Metabolism and Blood Flow in Hyperketonemia, E746-E751.
Hayes (2000) Am J Clin Nutr 72(6):1583-1584 "Medium-chain triacylglycerols may not raise cholesterol".
Henderson (2004) Medical Hypotheses 62:689-700 "High carbohydrate diets and Alzheimer's disease".
Hertz et al. (2000) Neurochemistry International 37:83-102 "Neuronal-astrocytic and cytosolic-mitochondrial metabolite trafficking during brain activation, hyperammonemia and energy deprivation".
Hiroyuki et al. Machine Translation of JP 06-287138, obtained Apr. 6, 2010, 9 pages.
Ho et al. (2004) The FASEB Journal express article 10.1096/fj.03-0978fje. Published online Mar. 19, 2004 "Diet-induced insulin resistance promotes amyloidosis in a transgenic mouse model of Alzheimer's disease".
Hoyer (1992) Molecular and Chemical Neuropathology 16:207-224 "Oxidative Energy Metabolism in Alzheimer Brain: Studies in Early-Onset and Late-Onset Cases".
Hoyer (1998) Journal of Neural Transmission 105:415-422 "Is sporadic Alzheimer disease the brain type of non-insulin dependent diabetes mellitus? A challenging hypothesis".
Huff and Strong (1987) Journal of Lipid Research 28:1118-1123 "Separation and isolation of human apolioproteins C-II, C-III0, C-III1, C-III2 by chromatofocusing on the Fast Protein Liquid Chromatography system".
Huttenlocher (1976) Pediatric Research 10:536-540 "Ketonemia and Seizures: Metabolic and Anticonvulsant Effects of Two Ketogenic Diets in Childhood Epilepsy".
Introducing Neurontin Capsules in a New Shape Ad (1996), 1 page.
Jandacek and Webb (1978) Chemistry and Physics of Lipids 22:163-176 "Physical Properties of Pure Sucrose Octaesters".
Jankovic and Aguilar (2008) Neuropsychiatric Disease and Treatment 4(4):743-757 "Currrent approaches to the treatment of Parkinson's disease".
Johnson et al. (1999) International Journal of Epidemiology 28:1102-1109 "Adult nutrient intake as a risk factor for Parkinson's disease".
Jolles et al. (1992) Journal of Neurochemistry 58(6):2326-2329 "Phosphatidylinositol Kinase Is Reduced in Alzheimer's Disease".
Jong et al. (1999) Arterioscler. Thromb. Vasc. Biol. 19:472-484 "Role of ApoCs in Lipoprotein Metabolism: Functional Differences Between ApoC1, ApoC2, and ApoC3".
Kalmijn et al. (1997) Annals of Neurology 42(5):776-782 "Dietary Fat Intake and the Risk of Incident Dementia in the Rotterdam Study".
Kashiwaya et al. (2000) PNAS 97(10):5440-5444 "D-β-Hydroxybutyrate protects neurons in models of Alzheimer's and Parkinson's disease".
Kidd (2008) Alternative Medicine Review 13(2):85-115 "Alzheimer's Disease, Amnestic Mild Cognitive Impairment, and Age-Associated Memory Impairment: Current Understanding and Progress Toward Integrative Prevention".
Kimball et al. (2002) J Appl Physiol 93:1168-1180 "Exercise Effects on Muscle Insulin Signaling and Action Invited Review: Role of insulin in translational control of protein synthesis in skeletal muscle by amino acids or exercise".
Klivenyi et al. (1999) Nature Medicine 5(3):347-350 "Neuroprotective effects of creatine in a transgenic animal model of amyotrophic lateral sclerosis".
Knouff et al. (1999) The Journal of Clinical Investigation 103(11):1579-1586 "APO E structure determines VLDL clearance and atherosclerosis risk in mice".
Kolanowski et al. (1994) Metabolism 43(2):180-185 "Stimulatory Influence of D (−)3-Hydroxybutyrate Feeding on Sympathetic Nervous System Activity in the Rat".

(56) References Cited

OTHER PUBLICATIONS

Koo et al. (1999) PNAS 96:9989-9990 "Amyloid diseases: Abnormal protein aggregation in neurodegeneration".
Kudo et al. (1995) The Journal of Biological Chemistry 270(29) 17513-17520 "High Rates of Fatty Acid Oxidation during Reperfusion of Ischemic Hearts are Associated with a Decrease in Malonyl-CoA Levels Due to an Increase in 5'-AMP-activated Protein Kinase Inhibition of Acetyl-CoA Carboxylase".
Lambert et al. (2005) J Neural Neurosurg Psychiatry 76:928-933 "Is there a relation between APOE expression and brain amyloid load in Alzheimer's disease?"
Lannert and Hoyer (1998) Behavorial Neuroscience 112(5):1199-1208 "Intracerebroventricular Administration of Streptozotocin Causes Long-Term Diminutions in Learning and Memory Abilities and in Cerebral Energy Metabolism in Adult Rats".
Lefevre and Aronson (2000) Pediatrics 105(4):46-52 "Ketogenic Diet for the Treatment of Refractory Epilepsy in Children: A Systematic Review of Efficacy".
Leino et al. (2001) Neurochemistry International 38:519-527 "Diet-induced ketosis increases monocarboxylate transporter (MCT1) levels in rat brain".
Ling et al. (2001) J. Med. Chem. 44:3141-3149 "Identification of Alkylidene Hydrazides as Glucagon Receptor Antagonists".
Liu and Barrett (2002) Am J Phsiol Endocinol Metab 283:E1105-E1112 "Human protein metabolism: its measurement and regulation".
Loktionov et al. (1999) Atherosclerosis 145:125-135 "Apolipoprotein E and methylenetetrahydrofolate reductase genetic polymorphisms in relation to other risk factors for cardiovascular disease in UK Caucasians and Black South Africans".
Loveman et al. (2006) Health Technology Assessment 10(1):1-375 "The Clinical and cost effectiveness of donepezil, rivastigmine, galantamine and memantine for Alzheimer's disease".
Mahley et al. (1999) Journal of Lipid Research 40:1933-1949 "Pathogens of type III hyperlipoproteinemia (dysbetalipoproteinemia): questions, quandries, and paradoxes".
Mak et al. (1999) Acta Pediatr. Sin 40:97-100 "Clinical Experience of Ketogenic Diet on Children with Refractory Epilepsy".
Mattson (1998) Science and Medicine March/April:17-25 "Experimental Models of Alzheimer's Disease".
McKhann et al. (1984) Neurology 34:939-943 "Clinical diagnosis of Alzheimer's Disease: Report of the NINCDS-ADRDA Work Group under the auspices of Department of Health and Human Services Task Force on Alzheimer's Disease".
Meier-Ruge et al. (1994) Gerontology 40:246-252 "Changes in Brain Glucose Metabolism as a Key to the Pathogenesis of Alzheimer's Disease".
Messier and Gagnon (1996) Behavioural Brain Research 75:1-11 "Glucose regulation and cognitive functions: relation to Alzheimer's disease and diabetes".
Michalik and Van Broeckhoven (2003) Human Molecular Genetics 12(2):R173-R186 "Pathogens of polyglutamine disorders: aggregation revisited".
Mitchell et al. (1995) Clin. Invest. Med. 18:3, 193-216 "Medical aspects of ketone body metabolism".
Moechars et al. (1999) The Journal of Biological Chemistry 274(10):6483-6492 "Early Phenotypic Changes in Transgenic Mice That Overexpress Different Mutants of Amyloid Precursor Protein in Brain".
Morris et al. (2003) Arch Neurol. 60:194-200 "Dietary Fats and the Risk of Incident Alzheimer Disease".
Murray et al. (1999) Harper's Biochemistry 25th Edition Table of Contents.
Nadal et al. (2002) Biochem J. 366:289-297 "Down-regulation of the mitochondrial 3-hydroxy-3-methylglutaryl-CoA synthase gene by insulin: the role of the forkhead trascription factor FKHRL1".
Nebeling and Lerner (1995) Journal of the American Dietetic Association 95(5):693-697 "Implementing a ketogenic diet based on medium-chain triglyceride oil in pediatric patients with cancer".
Neve and Robakis (1998) Trends Neurosci. 21:15-19 "Alzheimer's disease: a re-examination of the amyloid hypothesis".
Nishimura et al. (1999) Clinical Genetics 55:219-225 "Biology of presenilins as causative molecules for Alzheimer disease".
Nordberg (2004) Lancet Neurol 3:519-527 "PET imaging of amyloid in Alzheimer's disease".
Notice of Opposition sent Dec. 28, 2009 by the European Patent Office for 01930965.7.
NutritionData "Seeds, sunflower seed kernels, toasted, without salt" (one ounce); also available at http://www.nutritiondata.com/facts/nut-and-seed-products/3079/2; last viewed Apr. 6, 2010.
Odle (1997) J. Nutr.127:1061-1067 "New Insights into the Utilization of Medium-Chain Triglycerides by the Neonate: Observations from a Piglet Model".
Ogawa et al. (1996) Journal of Neurological Sciences 139:78-82 "Altered energy metabolism in Alzheimer's disease".
Osuntokun et al. (1995) Ann. Neurol. 38:463-465 "Lack of an Association Between Apolipoprotein E4 and Alzheimer's Disease in Elderly Nigerians".
Pegorier et al. (1988) Biochem Journal 249:801-806 "Fatty acid metabolism in hepatocytes isolates from rats adapted to high-fat diets containing long- or medium-chain triacylglycerols".
Pettegrew et al. (2000) Molecular Psychiatry 5: 616-632 "Acetyl-L-carnitine physical-chemical, metabolic, and therapeutic properties; relevance for its mode of action in Alzheimer's disease and geriatric depression".
Pi-Sunyer et al. (1969) Diabetes 18(2):96-100 "Insulin and Ketone Responses to Ingestion of Medium and Long-chain Triglycerides in Man".
Qureshi et al. (2000) The Journal of Biological Chemistry 275(47):36590-36595 "Activation of Insulin Signal Transduction Pathway and Anti-diabetic Activity of Small Molecule Insulin Receptor Activators".
Refolo et al. (2000) Neurobiology of Disease 7:321-331 "Hypercholesterolemia Accelerates the Alzheimer's Amyloid Pathology in a Transgenic Mouse Model".
Reger et al. (2004) Neurobiology of Aging 25:311-314 "Effects of β-hydroxybutyrate on congnition in memory-imparied adults".
Reiman et al. (1996) The New England Journal of Medicine 334(12):752-758 "Preclinical Evidence of Alzheimer's Disease in Persons Homozygous for the E4 Allele for Apolipoprotein E".
Robinson et al. (2004) Neurobiology of Aging 25:609-615 "Lessons from the AN 1792 Alzheimer vaccine: lest we forget".
Rocca et al. (1991) Annals of Neurology 30(3):381-390 "Frequency and distribution of alzheimer's disease in Europe: A collaborative study of 1980-1990 prevalence findings".
Roheim et al. (1979) Proc. Natl. Acad. Sci. 76(9):4646-4649 "Apolipoproteins in human cerebrospinal fluid".
Sato et al. (2003) Lifestyle-Related Diseases and Exercise 1208-1212 "Physical Exercise Improves Glucose Metabolism in Lifestyle-Related Diseases".
Schenk et al. (1999) Nature 400:173-177 "Immunization with amyloid-β attenuates Alzheimer-disease-like pathology in the PDAP mouse".
Schoonjans et al. (1999) FEBS Letters 452:160-164 "3-Hydroxy-3-methylglutaryl CoA reductase inhibitors reduce serum triglyceride level through modulation of apolipoprotein C-III and lipoprotein lipase".
Selkoe (1994) Journal of Neuropathology and Experimental Neurology 53(5):438-447 "Alzheimer's Disease: A Central Role for Amyloid".
Selkoe (1999) Nature 399:A23-A31 "Translating cell biology into therapeutic advances in Alzheimer's disease".
Selkoe (2001) Physiological Reviews 81(2):741-766 "Alzheimer's Disease: Genes, Proteins, and Therapy".
Selkoe (2004) Annals of Internal Medicine 140:627-638 "Alzheimer Disease: Mechanistic Understanding Predicts Novel Therapies".
Shah et al. (2000) Am J Physiol Endocrinol Metab 279:E715-E729 "4EBP1 and S6K1: translational intergration sites for nutritional and hormonal information in muscle".
Shi et al. (1999) The Journal of Biological Chemistry 274(14):9421-9426 "A Single Amino Acid Change (Substitution of Glutamate 3

(56) References Cited

OTHER PUBLICATIONS with Alanine) in the N-terminal Region of Rat Liver Canitine Palmitoyltransferase I Abolishes Malonyl-CoA Inhibition and High Affinity Binding".
Shie et al. (2002) NeuroReport 13(4):455-459 "Diet-induced hypercholesterolemia enhances brain A beta accumulation in transgenic mice".
Simpson and Davies (1994) Annals of Neurology 36(5):800-801 "Reduced Glucose Transporter Concentrations in Brains of Patients with Alzheimer's Disease".
Sirven et al. (1999) Epilepsia 40(12):1721-1726 "The Ketogenic Diet for Intractable Epilepsy in Adults: Preliminary Results".
Small et al. (2000) Proc. Natl. Acad. Sci. 97(11):6037-6042 "Cerebral metabolic and cognitive decline in persons at genetic risk for Alzheimer's disease".
Staels et al. (1998) Circulation 98:2088-2093 "Mechanism of Action of Fibrates on Lipid and Lipoprotein Metabolism".
Stella (2004) Expert Opin. Ther. Patents 14(3):277-280 "Prodrugs as therapeutics".
Stokin et al. (2005) Science 307:1282-1288 "Axonopathy and Transport Deficits Early in the Pathogenesis of Alzheimer's Disease".
Strittmatter and Roses (1996) Annu. Rev. Neurosci. 19:53-77 "Apolipoprotein E and Alzheimer's Disease".
Sugiura et al. (1996) Biochemical and Biophysical Research Communications 229:58-64 "2-Arachidonoylglycerol, a Putative Endogenous Cannabinoid Receptor Ligand, Induces Rapid, Transient Elevation of Intracellular Free Ca2+ in Neuroblastoma x Glioma Hybrid NG108-15 Cells".
Sugiura et al. (1997) J. Biochem. 122:890-895 "Is the Cannabinoid CB1 Receptor a 2-Arachidonoylglycerol Receptor? Structural Requirements for Triggering a Ca2+ Transient in NG108-15 Cells".
Sugiura et al. (1999) The Journal of Biological Chemistry 274(5):2794-2801 "Evidence That the Cannabinoid CB1 Receptor is a 2-Arachidonoylglycerol Receptor".
Sugiura et al. (2000) The Journal of Biological Chemistry 275(1):605-612 "Evidence That 2-Arachidonoylglycerol but Not N-Palmitoylethanolamine or Anandamide Is the Physiological Ligand for the Cannabinoid CB2 Receptor".
Swaab et al. (1998) Progress in Brain Research 117:343-377 "Reduced neuronal activity and reactivation in Alzheimer's disease".
Takada et al. (1991) Bull. Inst. Chem. Res., Kyoto Univ. 69(2):77-83 "Preparation of Cellobiose Octa(n-alkanoate)s and Their Thermal Properties".
Takada et al. (1992) Liquid Crystals 12(2):337-345 "Columnar liquid crystals in oligosaccharide derivatives II. Two types of discotic columnar liquid-crystalline phase of cellobiose alkanoates".
Takada et al. (1995) Liquid Crystals 19(4):441-448 "Discotic columnar liquid crystals in oligosaccharide derivatives III. Anomeric effects on the thermo-mesomorphic properties of cellobiose octaalkanoates".
Taylor et al. (2002) Science 296:1991-1995 "Toxic Proteins in Neurodegenerative Disease".
Testa (2004) Biochemical Pharmacology 68:2097-2106 "Prodrug research: futile or fertile?"
Thal et al. (1996) Neurology 47:705-711 "A 1-year multicenter placebo-controlled study of acetyl-L-carnitine in patients with Alzheimer's disease".
Thavendiranathan et al. (2000) Experimental Neurology 161:696-703 "The MCT Ketogenic Diet: Effects on Animal Seizure Models".
van Dongen et al. (2000) J Am Geriatr Soc. 48(10):1183-1194 "The efficacy of ginkgo for elderly people with dementia and age-associated memory impairment: new results of a randomized clinical trial".
van Dyck et al. (1998) Arch Neurol. 55:1460-1466 "Absence of an Apolipoprotein E4 Allele is Associated with Increased Parietal Regional Cerbral Blood Flow Asymmetry in Alzheimer Disease".
Van Wymlbeke (2001) Am. J. Clin. Nut. 74:620 "Substrate oxidation and control of food intake in men after a fat-substitute meal compared with meals supplemented with an isoenergetic load of carbohydrate, long-chain triacylglycerols, or medium-chain triacylglycerols".

Veech et al. (2001) IUBMB Life 51:241-247 "Ketone Bodies, Potential Therapeutic Uses".
Veneman et al. (1994) Diabetes 43:1311-1317 "Effect of Hyperketonemia and Hyperlacticacidemia on Symptoms, Cognitive Dysfunction, and Counterregulatory Hormone Responses During Hypoglycemia in Normal Humans".
Wang et al. (2000) The Journal of Biological Chemistry 275(27):20782-20786 "Abnormal Sodium Stimulation of Carnitine Transport in Primary Carnitine Deficiency".
Wang et al. (2005) The FASEB Journal Published Online 1-18 "Caloric Restriciton Attenuates β-amyloid Neuropathology in a mouse model of Alzheimer's disease".
Winocur and Greenwood (1999) Behavioural Brain Research 101:153-161 "The effects of high fat diets and environmental influences on cognitive performance in rats".
Witters et al. (1988) Proc. Natl. Acad. Sci. 85:5473-5477 "Insulin stimulates the dephosphorylation and activation of acetyl-CoA carboxylase".
Wolff (1995) Burger's Medicinal Chemistry and Drug Discovery Fifth Edition, vol. 1:975-977 "Principles and Practice".
Wu et al. (2003) Neuroscience 119:365-375 "A Saturated-Fat Diet Aggravates the Outcome of Traumatic Brain Injury on Hippocampal Plasticity and Cognitive Function by Reducing Brain-Derived Neurotrophic Fator".
Yamamoto et al. (2000) Cell 101:57-66 "Reversal of Neuropathology and Motor Dysfunction in a Conditional Model of Huntington's Disease".
York et al. (1997) Carb. Research, Elsevier Scientific Publishing Co. 300(3):199-206 "Determination of the absolute configuration of monosaccharides by $^1$H NMR spectroscopy of their per-0-(S)-2-methylbutyrate derivatives".
Zekraoui et al. (1997) Human Biology 69(4):575 "High frequency of the apolipoprotein E4 allele in African pygmies and most of the African populations in Sub-Saharan Africa".
Zhao et al. (2004) Pediatric Research 55(3):498-506 "Detrimental Effects of the Ketogenic Diet on Cognitive Function in Rats".
Zhou et al. (1998) Molecular Endocrinology 12:1594-1604 "Nuclear Receptors Have Distinct Affinities for Coactivators: Characterization by Fluorescense Resonance Energy Transfer".
Zief (1950) J. of Amer. Chern. Soc. 72:1137-40 "Unsaturated esters of sucrose".
Zubenko et al. (1999) Biol Psychiatry 45:731-736 "Reductions in Brain Phosphatidylinositol Kinase Activities in Alzheimer's Disease".
Birkhahn et al. (1986) Journal of Nutrition 116:851-864 "Total Parenteral Feeding of Rats with an Acetoacetate Monoglyceride and Glucose Mixture".
Nagayama et al. (1990) Japanese Journal of Surgical Metabolism and Nutrition 24:521-529 "Enteral Nutrition with Monoacetoacetin as an Energy and Ketone Body Sources in Rats".
U.S. Appl. No. 09/845,741, filed May 1, 2001, Henderson.
U.S. Appl. No. 11/021,920, filed Dec. 22, 2004, Henderson.
Australian Examination Report for Application No. 2009266869 dated Sep. 30, 2014.
Bartl et al. "Disorder-specific effects of polymorphisms at opposing ends of the Insulin Degrading Enzyme gene" BMC Medical Genetics, 2011, vol. 12, Article 151, 8 pages.
Edland et al. 2003 Neuroscience Letters 345 p. 21-24 "Insulin degrading enzyme (IDE) genetic variants and risk of Alzheimer's disease: evidence of effect".
Experimental Drug Ketasyn™ (AC-1202) Treats Alzheimer's as Diabetes of the Brain, medicalnewstoday.com URL: http://www.medicalnewstoday.com/printerfriendlynews.php?newsid=75335, (2014).
Grupe et al. 2006 Am J of Human Genetics 78 p. 78-88 "A scan of chromosome 10 identifies a novel locus showing strong association with late-onset Alzheimer disease".
Hashim et al. (2014) "Ketone Body Therapy: From the Ketogenic Diet to the Oral Administration of Ketone Ester" J of Lipid Research pp. 1-35.
Henderson et al. "Pharmacogenetic analysis of the effects of polymorphisms in APOE, IDE and IL1B on a ketone body based therapeutic on cognition in mild to moderate Alzheimer's disease; a (56) References Cited

OTHER PUBLICATIONS randomized, double-blind, placebo-controlled study" BMC Medical Genetics, 2011, vol. 12, Article 137, 14 pages.
Henderson et al. 2009 Nutrition & Metabolism 6:31 "Study of the ketogenic agent AC-I202 in mild to moderate Alzheimer's disease".
International Preliminary Report on Patentability prepared by the International Bureau of WIPO for PCT/US2008/071817, mailed Feb. 11, 2010, 6 pages.
International Search Report and Written Opinion prepared by the USPTO as International Searching Authority (ISA/US) for PCT/US2008/071817, mailed Jan. 12, 2009, 12 pages.
Japanese Office Action for Application No. 2010-520202 dated Mar. 4, 2014.
Japanese Office Action for Application No. 2011-516888 dated Feb. 5, 2014.
Japanese Office Action for Application No. 2012-267035 dated Feb. 21, 2014.
Kalaria et al. (1992) Annals of Neurology 32(4):583-586 "Carnitine Acetyltransferase Activity in the Human Brain and Its Microvessels is Decreased in Alzheimer's Disease".
Karmee et al., (2005) "Rapid and Simple Method of Monoacylation of Polyols by β-Ketoesters Using Microwave Irradiation" Synthetic Communications, 35: 1151-1160.
Leadbeater et al., (2007) "Probing the effects of microwave irradiation on enzyme-catalysed organic transformations: the case of lipase-catalysed transesterification reactions", Org & Biomolecular Chem, 5;7: 1052-1055.
Messier 2005 Neural Plast 12:4 p. 311-328 "The Role of Insulin, Insulin Growth Factor, and Insulin-Degrading Enzyme in Brain Aging and Alzheimer's Disease".
Ogden et al. (2004) Advance Data from Vital and Health Statistics 347:1-18 "Mean Body Weight, Height, and Body Mass Index, United States 1960-2002".
Poirier et al. (1995) Proc. Natl. Acad. Sci. 92:12260-12264 "Apolipoprotein E4 allele as a predictor of cholinergic deficits and treatment outcome in Alzheimer disease".
Risner et al. 2006 Pharmacogenomics J 6 p. 246-254 "Efficacy of rosiglitazone in a genetically defined population with mild-to-moderate Alzheimer's disease".
U.S. Appl. No. 11/331,673, Office Action dated Oct. 10, 2008, 30 pages.
Wegman et al. 2005 Breast Cancer Research 7:R284-R290 "Genotype of metabolic enzymes and the benefit of tamoxifen in postmenopausal breast cancer patients".
Yadav et al. (2004) "Synergism between microwave and enzyme catalysis in intensification of reactions and selectivities: transesterification of methyl acetoacetate with alcohols" J. Molecular Catalysis A: Chem 223; 1-2: 51-56.
Yadav et al. (2005) "Lipase catalyzed transesterification of methyl acetoacetate with n-butanol", J. Molecular Catalysis B: Enzymatic 32: 107-113.
McGleenon, B. M. et al. (1999) "Acetylcholinesterase inhibitors in Alzheimer's disease" J. Clin. Pharmacol, 48:471-480.
Prince et al. (2003) "Genetic Variation in a Haplotype Block Spanning IDS Influences Alzheimer Disease" Human Mutation, 22:363-371.
Ertekin-Taner et al. (2004) "Genetic Variants in a Haplotype Block Spanning IDS Are Significantly Associated with Plasma Aβ42 Levels and Risk for Alzheimer Disease" Human Mutation, 23:334-342.
Nagayama and Birkhahn (1987) Japanese Journal of Surgical Metabolism and Nutrition 20:393-399 "Intravenous Tolerance Test of new Synthetic Energy Source (monoacetoacetin: MA in Rats".
Nishiguchi et al. (2001) The Japanese Journal of Parenteral and Enteral Nutrition 23(6):327-332 "Clinical aspect of nutritional therapy using ketone body".
Nagayama and Birkhahn (1987) The Japanese Journal of Gastroenterological Surgery 20(5):1087-1092 "Effect to Colonic Anastomosis in Postoperative TPN with Monoacetoacetin as New Synthetic Energy Source in Rats".
Japanese Office Action for application 2011-516889 dated Sep. 17, 2013; English Translation of Office Action.

* cited by examiner

MONOGLYCERIDE OF ACETOACETATE AND DERIVATIVES FOR THE TREATMENT OF NEUROLOGICAL DISORDERS

RELATED APPLICATIONS

This application is a 35 USC §371 of PCT Application Serial No. PCT/US2009/049609, filed Jul. 2, 2009, currently pending, entitled "Monoglyceride of Acetoacetate and Derivatives for the Treatment of Neurological Disorders," which claims priority to U.S. Provisional Application No. 61/078,214, filed Jul. 3, 2008, entitled "Monoglyceride of Acetoacetate and Derivatives for the Treatment of Neurological Disorders," which are each incorporated herein in their entirety by reference.

FIELD OF THE INVENTION

This invention relates to methods of for the treatment, prevention, inhibition or alleviation of neurological diseases associated with neuronal hypometabolism, such as Alzheimer's disease, Parkinson's disease, Friedreich's Ataxia (FRDA), GLUT1-deficient Epilepsy, Leprechaunism and Rabson-Mendenhall Syndrome, Coronary Arterial Bypass Graft (CABG) dementia, anesthesia induced memory loss, age associated memory impairment (AAMI), Traumatic Brain Injury (TBI), Huntington's disease and many others.

BACKGROUND

Alzheimer's Disease

Alzheimer's disease (AD) is a progressive neurodegenerative disorder that primarily affects the elderly. In 1984, Blass and Zemcov (Blass and Zemcov 1984) proposed that AD resulted from a decreased metabolic rate in sub-populations of cholinergic neurons. However, it has become clear that AD is not restricted to cholinergic systems, but involves many types of transmitter systems, and several discrete brain regions. The decreased metabolic rate appears to be related to decreases in glucose utilization. Brain imaging techniques have revealed decreased uptake of radiolabeled glucose in the brains of AD patients, and these defects can be detected well before clinical signs of dementia occur (Reiman, Caselli et al. 1996). Measurements of cerebral glucose metabolism indicate that glucose metabolism is reduced 20-40% in AD resulting in critically low levels of ATP.

The cause of the decreased glucose metabolism remains uncertain, but may be related to processing of the amyloid precursor protein (APP). Mutations that alter the processing of APP have been implicated in early onset AD. Early onset cases occur before the age of 60 and in many cases have been associated with mutations in three genes: APP, presenilin 1 (PS1) and presenilin 2 (PS2). Mutations in these genes lead to aberrant processing of the APP protein (for review see (Selkoe 1999)). Where examined, these pathological mutations result in early defects in cerebral glucose metabolism. Individuals harboring a double mutation at APP670/671 (the "Swedish mutation") exhibit pathological decreases in glucose metabolism in temporal lobes, often before clinical manifestations of dementia are evident. Mice carrying an APP V717F transgene exhibit regional defects in cerebral glucose metabolism. Also, mutations in the presenilin genes may directly increase susceptibility to glucose deprivation.

Attempts to compensate for reduced cerebral metabolic rates in AD have met with some success. Elevation of serum ketone body levels in AD patients raises cognitive scores (Reger, Henderson et al. 2004) and USP. However, this reported method requires administration of large amounts of fat to generate the sufficient levels of ketone bodies. Therefore, a need exists for compounds that can elevate ketone levels without large fat consumption.

Parkinson Disease (PD)

Parkinson's disease (PD) is a progressive neurodegenerative disorder that is the second most common neurodegenerative disease after Alzheimer's disease. The estimated prevalence of PD is 0.3 percent in the general U.S. population and a prevalence of 4 to 5 percent in those older than 85 years. PD is characterized by motor abnormalities, including tremors, muscle stiffness, lack of voluntary movements, and postural instability. A primary neuropathological feature of PD is the loss of dopaminergic neurons in the substantia nigra pars compacta (SNpc) and the presence of eosinophilic intracytoplasmic inclusions (Lewy bodies) in the residual dopaminergic neurons.

Current treatments for PD include monoamine oxidase-B (MAO-B) inhibitors, amantadine (Symmetrel), or anticholinergics. Such agents may modestly improve mild symptoms. However, due to large scale cell loss the American Academy of Neurology (AAN) recommends levodopa or a dopamine agonist when dopaminergic treatment is required. Typically, levadopa is given to those who need to improve motor disability, while dopamine agonists are given to those who need to decrease motor complications. In general, a dopamine agonist is initiated in younger patients with mild disease, whereas levodopa is initiated in older patients with severe motor symptoms.

While treatment for PD in the early stages can be considered relatively successful, after about five years of treatment with levodopa, about 40 percent of patients develop dyskinesia (i.e., involuntary choreiform or stereotypic movements involving the head, trunk, limbs, and, occasionally, the respiratory muscles). Patients experience a "wearing-off" effect characterized by a weakening of the benefit from individual levodopa doses, causing the parkinsonian symptoms to reemerge. Patients may also experience an "on-off" effect characterized by unpredictable, abrupt fluctuations in motor state. Therefore, there exists a need for more effective treatments for PD and in particular for treatments that are neuroprotective.

While the cause of sporadic PD is uncertain, several lines of evidence suggest that defects in oxidative phosphorylation may contribute to its pathogenesis. For example, 1-methyl-4-phenyl-1,2,3,6-tetrahydropyridine (MPTP), blocks complex I (NADH-ubiquinone oxidoreductase) of the mitochondrial electron transport chain, and causes the loss of dopaminergic neurons and the typical symptoms of PD. Reduction in complex I activity has also been reported in PD tissues. This defect is not confined only to the brain but has also been found in platelets from PD patients.

D-β-Hydroxybutyrate (BHB) is a ketone body produced by hepatocytes and, to a lesser extent, by astrocytes. BHB acts as an alternative source of energy in the brain when glucose supply is limited such as during starvation. BHB has been found to protect from MPTP-related complex I inhibition, by enhancing oxidative phosphorylation {Tieu, 2003#295}.

Friedreich's Ataxia (FRDA)

FRDA is a recessive disease characterized by progressive ataxia, hypertrophic cardiomyopathy, early onset of insulin-resistant diabetes, invalidism, and premature death. FRDA is a genetic disorder caused by a deficiency of frataxin, a 210 amino acid nuclear-encoded mitochondrial protein. Low levels of the protein are due to the expansion of an intronic GAA repeat, leading to decreased mRNA levels. FRDA patients show a decrease in the activity of the mitochondrial enzyme aconitase. Aconitase is responsible for conversion of citrate to isocitrate, the first step in the Krebs (also known as the citric acid or TCA cycle). Deficiency of frataxin in human patients is thought to lead primarily to defects in the TCA cycle.

Recent work shows that elevation of blood ketone bodies, a normal response to fasting, can increase mitochondrial citrate and isocitrate levels, thus overcoming the block in aconitase found in FRDA. A ketone body-based therapy could provide an effective treatment for this group of patients.

GLUT1-Deficient Epilepsy

GLUT1-deficient Epilepsy is characterized by infantile seizures, delayed development, and acquired microcephaly with mental retardation. GLUT1-deficient epilepsy results from several types of mutation in the gene of GLUT1. Glucose transporter 1 (GLUT1) is the major protein responsible for the transport of glucose from bloodstream into the brain. Under standard dietary conditions, the brain is almost entirely dependent upon blood glucose for energy. However, under some circumstances, such as starvation, ketone bodies can provide a source of energy different from glucose. Ketone bodies do not rely on GLUT1 for transport into the brain and therefore may provide energy in GLUT1-deficient syndrome. Ketone body therapy may therefore become a practical method for lifelong treatment of these patients.

Leprechaunism and Rabson-Mendenhall Syndrome

Leprechaunism and Rabson-Mendenhall syndrome are rare disease characterized by insulin resistance, persistent hyperglycemia and retardation of growth. Subjects rarely survive past 20 years of age. These syndromes result from mutations in the insulin receptor gene, which lower the receptors affinity for insulin. The current treatment consists of administration of increasing doses of insulin (up to several thousand units per day). This treatment yields only weak results due to the poor binding of insulin to its receptor. Ketone bodies have been shown to mimic the effects of insulin's stimulation of the PDH multienzyme complex, thereby increasing the Krebs TCA cycle metabolite levels, increasing the energy output in the form of ATP, and enhancing metabolic efficiency. A ketone-rich, or ketogenic diet may prove an effective treatment of these conditions Other Diseases and Syndromes A great number of other diseases and syndromes are associated with decreased metabolism. Such conditions include Coronary Arterial Bypass Graft (CABG) dementia, age associated memory impairment, anesthesia induced memory loss, Traumatic brain injury, Huntington's disease and many other. It is apparent that a metabolic intervention may aid people suffering from such afflictions.

Unmet Need

While ketone body based therapies may be appropriate for such diseases, current methods are impractical or inadequate. Ketogenic diets require continuous strict adherence to low carbohydrate intake which makes them difficult to comply with.

In 1979 Birkhahn et al., ((Birkhahn, McMenamy et al. 1979)) described the synthesis of the monoglyceride of acetoacetate which they called monoacetoacetin (MA). In subsequent studies (1986), Birkhahn, McMemany and Border fed monoacetoacetin intravenously to rats to examine if monoacetoacetin was a suitable replacement energy source (Birkhahn, Askari et al. 1986).

Additional studies on monoacetoacetin were done by Hirakawa and co-authors extending work by Birkhahn. In a study published in 2004 Sawai et. al. examined the effect of monoacetoacetin as a source of energy for cell cultures of several gastric cancer cell lines. (Sawai, Yashiro et al. 2004) (Takahata, Ohira et al. 2004).

It can be seen that none of the published prior art relates to the use of monoacetoacetin for the treatment of neurological disorders such as Alzheimer's disease, Parkinson's disease, Friedreich's Ataxia (FRDA), GLUT1-deficient Epilepsy, Leprechaunism and Rabson-Mendenhall Syndrome, Coronary Arterial Bypass Graft (CABG) dementia, anesthesia induced memory loss, age associated memory impairment, Traumatic brain injury, Huntington's disease or Parkinson's disease. It is the novel insight of the present invention that monoacetoacetin could be used to treat such conditions.

Several patent applications were filed on related compounds by Birkhahn and co-inventors. U.S. Pat. No. 5,420,335 entitled "Parenteral nutrients based on water soluble glycerol bisacetoacetates" was issued on May 30, 1995. U.S. Pat. No. 5,693,850 entitled "Nutritive water soluble glycerol esters of hydroxybutyric acid" was issued Dec. 2, 1997. A series of patents and applications relate to similar compounds for the treatment of neurodegenerative disorders by the inventor Richard Veech, these include U.S. Pat. Nos. 6,323,237, 6,316,038, and 6207856 as well as several applications including: US2004/0266872, US2004/0171671 and US2006/0280721. However, it is noted that the Veech patents teach that since "neither 1,3 butanediol, which forms acetoacetate, nor glycerol, which is a precursor of glucose, is part of the normal redox couple, D-β-hydroxybutyrate" and that "a physiological ratio of ketones should be given. If it is not, in the whole animal, the liver will adjust the ratio of ketones in accordance with its own mitochondrial free [NAD+]/[NADH]. If an abnormal ratio of ketones is given pathological consequences are a distinct possibility". See, e.g., US2004/0171671 Paragraph [0054].

Therefore, it can be seen that the present invention shows that monoacetoacetin and other acetoacetate esters, administered in the lack of a source of hydroxybutyric acid or corresponding salt, may be used to effectively treat neurodegenerative disorders. Therefore, the unmet needs discussed above may be addressed.

All U.S. patents and patent applications referenced herein are incorporated by reference herein in their entireties. A partial list of those patents and applications referenced herein include, for example, U.S. Ser. No. 60/953,074, "Genomic testing in Alzheimer's disease and other diseases associated with reduced neuronal metabolism", filed Jul. 31, 2007; U.S. Ser. No. 60/917,886, "Inhibitors of Acetyl-CoA Carboxylase for Treatment of Hypometabolism", filed May 14, 2007; U.S. Ser. No. 11/123,706, "Method for Reducing Levels of Disease Associated Proteins", filed May 3, 2005; U.S. Ser. No. 11/424,429, "Method To Reduce Oxidative Damage And Improve Mitochondrial Efficiency", filed Jun. 15, 2006; U.S. Ser. No. 10/546,976, "Novel-Chemical Entities and Methods for their Use in Treatment of Metabolic Disorders", filed Aug. 25, 2005; U.S. Ser. No. 09/845,741, filed May 1, 2001; U.S. Ser. No. 10/152,147, filed Dec. 28, 2004, now U.S. Pat. No. 6,835,750; U.S. Ser. No. 11/021,920, filed Dec. 22, 2004; U.S. Ser. No. 11/331,673, filed Jan. 13, 2006; U.S. Ser. No. 11/611,114, filed Dec. 14, 2006; and U.S. Ser. No. 11/771,431, filed Jun. 29, 2007.

SUMMARY OF THE INVENTION

The present invention includes a method of treatment of a disease associated with hypometabolism, which comprises administering to a subject suffering from a disease associated with hypometabolism a composition comprising an effective amount of a compound of Wherein R represents independently either a hydroxyl or an ester of an acetoacetate, or a pharmaceutically acceptable salt thereof, wherein the composition lacks a source of D-β-hydroxybutyric acid or its corresponding salt, in an amount effective to elevate the patient's blood level of ketone bodies.

In another embodiment, the elevated level of ketone bodies are present in the patient's blood in a normal range of a physiologic ratio of D-β-hydroxybutyrate and acetoacetate. The diseases which may be associated with hypometabolism include Alzheimer's disease, Parkinson's disease, Friedreich's Ataxia, GLUT1-deficient Epilepsy, Leprechaunism and Rabson-Mendenhall Syndrome, Coronary Arterial Bypass Graft dementia, anesthesia induced memory loss, age associated memory impairment, or Huntington's disease. In one embodiment, a compound of formula I are administered at a dose in the range of 0.1 g/kg/day to 10 g/kg/day.

In one embodiment, the patient's blood level of ketone bodies is elevated to from 0.2 mM to 20 mM at about two hours post administration. In one embodiment, Formula I is monoacetoacetin.

The methods of the present invention also include the further step of determining the ApoE status of the mammal and selecting a mammal for treatment if the mammal is ApoE4 (−). In other embodiments, a second composition is administered, wherein said composition comprises a carbohydrate source. In one embodiment, the carbohydrate source is glucose. In another embodiment, the composition further comprises a carbohydrate source. The carbohydrate source may be glucose.

DESCRIPTION OF THE INVENTION

There is a great need for treatment of disorders such as Alzheimer's disease, Parkinson's disease, Friedreich's Ataxia (FRDA), GLUT1-deficient Epilepsy, Leprechaunism and Rabson-Mendenhall Syndrome, Coronary Arterial Bypass Graft (CABG) dementia, anesthesia induced memory loss, age associated memory impairment, Traumatic Brain Injury, Huntington's disease and many others. For example, current treatments for Alzheimer's disease do little to slow or treat the disease. The use of ketone body precursors such as the compositions of the present invention, including such compounds as monoacetoacetin as described in the present invention will meet a great unmet medical need.

The inventor has previously shown that induction of ketosis by oral administration of medium chain triglycerides (MCT) improves the cognitive performance of probable mild to moderate Alzheimer's disease subjects (U.S. Pat. No. 6,835,750; Reger, 2004 #136. However, this treatment requires large amounts of MCT to be administered and may cause some intestinal distress. In the present application, the inventor discloses a new invention that solves many of the problems associated with administration of MCT.

The present invention describes inducing hyperketonemia by administration to a mammal a composition comprising an effective amount of a compound of formula I:

wherein R represents independently either a hydroxyl or an ester of an acetoacetate, or a precursor of acetoacetate, or a pharmaceutically acceptable salt thereof, wherein the composition lacks a source of D-β-hydroxybutyric acid or its corresponding salt, in an amount effective to elevate the patient's blood level of ketone bodies. Compounds of formula I also are useful as a method of treatment of a disease associated with hypometabolism. In one embodiment, the present invention includes oral and intravenous administration of monoacetoacetin (2,3-dihydroxypropyl 3-oxobutanoate). In another embodiment, the present invention includes glyceryl bisacetoacetate (diglyceride of acetoacetate). In another embodiment, the present invention includes the triglyceride of acetoacetate. Compounds according to Formula I elevate circulating ketone body levels in a mammal and that this is useful for treating neurodegenerative disorders and disorders of hypometabolism.

In some embodiments, a disease associated with hypometabolism can be any of the following: Alzheimer's disease, Parkinson's disease, Friedreich's Ataxia, GLUT1-deficient Epilepsy, Leprechaunism and Rabson-Mendenhall Syndrome, Coronary Arterial Bypass Graft dementia, anesthesia induced memory loss, age associated memory impairment, Traumatic brain injury, or Huntington's disease. In one embodiment, the disease associated with hypometabolism to be treated is Alzheimer's disease.

Methods to make monoacetoacetin and other compounds are known in the art.

The inventors have shown that when fed orally, monoacetoacetin elevates serum ketone bodies, in particular β-hydroxybutyrate (βHB). Surprisingly, feeding a precursor of acetoacetate, such as monoacetoacetin which breaks down to acetoacetate in vivo, has been shown to be efficacious for treatment of a neurological disorder, despite the teaching of the art which teaches that administration of a precursor of acetoacetate without a source of its corresponding redox couple, D-β-hydroxybutyrate, could lead to pathologic consequences.

Ketone bodies serve a critical role in the development and health of cerebral neurons. Numerous studies have shown that the preferred substrates for the developing mammalian neonatal brain are ketone bodies (for review, see reference (Edmond, 1992 #43}). There is a large body of evidence demonstrating that ketone bodies are used in a concentration dependent manner by the adult human brain, even in the elderly. The ability of ketone bodies to supplement glucose in the brain has been used to treat conditions of low glucose availability to the brain. GLUT-1 is a constitutive glucose transporter that transports glucose into the central nervous system (CNS). The high glucose requirement of the brain requires that two functional copies of the Glut-1 gene be present. If one copy of Glut-1 is non-functional this results in GLUT-1 deficiency syndrome. The resulting low glucose levels during development lead to infant seizures, delayed development and microcephaly. Partial relief of these symptoms can be achieved by increasing serum ketone levels by administration of a ketogenic diet.

These compounds can mimic the effect of increasing oxidation of fatty acids and include but are not limited to compounds of Formula I, such as monoacetoacetin. A precursor of acetoacetate includes compounds that when administered directly give rise to acetoacetate. Such compounds may give rise to acetoacetate by the action of enzymes that act on the precursor compounds to release acetoacetate, or by change in pH, temperature, or mechanical action. Such compounds include but are not limited to, dimmers, trimers or other oligomers of acetoacetate; esters of acetoacetate and saccharides, including other linkages such as amides and sulfur bonds.

It is the novel insight of the inventor that induction of ketosis via the inventive compositions will alleviate conditions associated with decreased glucose utilization.

With regard to epilepsy, the prior art provides descriptions of ketogenic diets in which fat is high and carbohydrates are limited. In summary, the rationale of such diets is that intake of high amounts of fat, whether long-chain or medium-chain triglycerides, can increase blood ketone levels in the context of a highly regimented diet in which carbohydrate levels are absent or limited. Limitation of carbohydrate and insulin are believed to prevent re-esterification in adipose tissue. In contrast to the prior art, the present invention provides for and claims the administration of compounds of Formula I, such as, for example, monoacetoacetin, outside of the context of the ketogenic diet. Furthermore, the EXAMPLES section below provides exemplary formulations which include carbohydrates.

In some embodiments, the inventive compounds may be co-administered with a carbohydrate source or co-formulated with a carbohydrate source. A carbohydrate source can include more than one type of carbohydrate. Carbohydrates or saccharides are generally simple molecules that are straight-chain aldehydes or ketones with many hydroxyl groups added, usually one on each carbon atom that is not part of the aldehyde or ketone functional group. A carbohydrate may be a monosaccharide, a disaccharide, a polysaccharide and/or an oligosaccharide. Appropriate carbohydrates for the invention are carbohydrates, which are, upon digestion in a mammal, capable of yielding at least a portion of the carbohydrate as a monosaccharide. In one embodiment, the carbohydrate is a monosaccharide, and optionally is glucose, fructose and/or galactose. In another embodiment, the carbohydrate is a disaccharide, and optionally is sucrose and/or lactose.

Further benefit can be derived from formulation of a pharmaceutical composition, including a first composition and/or second composition, which include metabolic adjuvants. Metabolic adjuvants include vitamins, minerals, antioxidants and other related compounds. Such compounds may be chosen from a list that includes but is not limited to; ascorbic acid, biotin, calcitriol, cobalamin, folic acid, niacin, pantothenic acid, pyridoxine, retinol, retinal (retinaldehyde), retinoic acid, riboflavin, thiamin, α-tocopherol, phytylmenaquinone, multiprenylmenaquinone, calcium, magnesium, sodium, aluminum, zinc, potassium, chromium, vanadium, selenium, phosphorous, manganese, iron, fluorine, copper, cobalt, molybdenum, iodine. Accordingly a combination of ingredients chosen from: metabolic adjuvants, compounds that increase ketone body levels, and TCA cycle intermediates, will prove beneficial for treatment and prevention of diseases associated with decreased metabolism, including Alzheimer's disease, Parkinson's disease, TBI, Huntington's disease, and epilepsy.

Administration of the compositions of the invention can be on an as-needed or as-desired basis. The composition can be administered once monthly, once weekly, daily, or more than once daily. Similarly, administration can be every other day, week, or month, every third day, week, or month, every fourth day, week, or month, and the like. Administration can be multiple times per day. When utilized as a supplement to ordinary dietary requirements, the composition may be administered directly to the mammal or otherwise contacted with or admixed with daily food or beverage. When utilized as a daily food or beverage, administration techniques will be known to those of skill in the art. Administration can also be carried out on a regular basis, for example, as part of a treatment regimen in the mammal. A treatment regimen may comprise causing the regular ingestion by the mammal of an inventive composition in an amount effective to enhance characteristics as defined above. Regular ingestion can be once a day, or two, three, four, or more times per day, on a daily or weekly basis. Similarly, regular administration can be every other day or week, every third day or week, every fourth day or week, every fifth day or week, every sixth day or week, and in such a regimen, administration can be multiple times per day. The goal of regular administration is to provide the mammal with optimal dose of any of the inventive compositions, as exemplified herein.

The compositions provided herein, are, in one embodiment, intended for "long term" consumption, sometimes referred to herein as for "extended" periods. Long-term administration as used herein generally refers to periods in excess of one month. Periods of longer than two, three, or four months comprise one embodiment of the instant invention. Also included are embodiments comprising more extended periods that include longer than 5, 6, 7, 8, 9, or 10 months. Periods in excess of 11 months or one year are also included. Longer-term use extending over 1, 2, 3, 4, 5, 6, 7, 8, 10, 12, 14, 16, 18, 20 or more years is also contemplated. In some cases, it is envisioned that the patient would continue consuming the compositions for the remainder of its life, on a regular basis as discussed hereinabove. Regular basis as used herein refers to at least weekly dosing with or consumption of the compositions. More frequent dosing or consumption, such as twice or thrice weekly are also included. Also included are regimens that include at least once daily consumption. The skilled artisan will appreciate that the blood (urine or cerebral spinal fluid) levels of ketone bodies, or a specific ketone body, achieved may be a valuable measure for determining dosing frequency. Any frequency, regardless of whether expressly exemplified herein, that allows maintenance of a blood level of the measured compound within acceptable ranges can be considered useful herein. The skilled artisan will appreciate that dosing frequency will be a function of the composition that is being consumed or administered, and some compositions may require more or less frequent administration to maintain a desired blood level of the measured compound (e.g., a ketone body).

Generally, an effective amount is an amount effective to either (1) reduce the symptoms of the disease sought to be treated or (2) induce a pharmacological change relevant to treating the disease sought to be treated. For example, for Alzheimer's disease, an effective amount includes an amount effective to: increase cognitive scores; slow the progression of dementia; or increase the life expectancy of the affected patient. Effective amount also refers to an amount of compound or composition as described herein that is effective to achieve a particular biological result. Effectiveness for treatment of some of the aforementioned conditions may be assessed by improved results for at least one neuropsychological test, for example, and includes any neuropsychological tests known in the art for assessing a disease associated with hypometabolism including Alzheimer's disease, Parkinson's disease, Friedreich's Ataxia, GLUT1-deficient Epilepsy, Leprechaunism and Rabson-Mendenhall Syndrome, Coronary Arterial Bypass Graft dementia, anesthesia induced memory loss, age associated memory impairment, or Huntington's disease. Examples of such neuropsychological tests include ADAS-cog, MMSE, Stroop Color Word Interference Task, Logical Memory subtest of the Wechsler Memory Scale-III, Clinician's Dementia Rating, and Clinician's Interview Based Impression of Change. Effectiveness for treatment of the aforementioned conditions include improvements in the proper physiological activity of the brain, such as mental stability, memory/recall abilities, problem solving abilities, reasoning abilities, thinking abilities, judging abilities, capacity for learning, perception, intuition, awareness, attention, as measured by any means suitable in the art.

Decline of any of the foregoing categories or specific types of qualities or functions in an individual is generally the opposite of an improvement or enhancement in the quality or function. An "effective amount" (as discussed above) of a composition of the invention may be an amount required to prevent decline, to reduce the extent or rate of decline, or delay the onset or progression of a decline, or lead to an improvement from a previous decline. Prevention, reduction, or delay of a decline can be considered relative to a cohort that does not receive the treatment. Prevention, reduction or delay of a decline may also be measured and considered on an individual basis, or in some embodiments, on a population basis.

In a preferred embodiment, the ketogenic compound is provided in administratively convenient formulations of the compositions including dosage units incorporated into a variety of containers. Dosages of the ketogenic compound, such as monoacetoacetein, are preferably administered in an effective amount, in order to produce ketone body concentrations sufficient to increase the cognitive ability of patients afflicted with a disease associated with hypometabolism such as Alzheimer's disease, Parkinson's disease, Friedreich's Ataxia, GLUT1-deficient Epilepsy, Leprechaunism and Rabson-Mendenhall Syndrome, Coronary Arterial Bypass Graft dementia, anesthesia induced memory loss, age associate memory impairment, Traumatic brain injury, or Huntington's disease, as discussed hereinabove.

In one embodiment, the ketogenic compounds are administered orally. In another embodiment, the ketogenic compounds are administered intravenously. Oral administration of, for example, monoacetoacetin and/or other ketogenic compound preparations is known in the art.

In one embodiment, any of the compositions of the invention increase the circulating concentration of at least one type of ketone body in the mammal or patient. In one embodiment, the circulating ketone body is D-β-hydroxybutyrate. In another embodiment, the circulating ketone body is an equimolar mixture of the normal redox couple, D-β-hydroxybutyrate/acetoacetate. In one embodiment, the liver adjusts the ratio of ketones in accordance with its own mitochondrial free [NAD+]/[NADH]. The amount of circulating ketone bodies (or body) can be measured at a number of times post administration, and in one embodiment, is measured at a time predicted to be near the peak concentration in the blood, but circulating ketone body can also measured before or after the predicted peak blood concentration level. In some embodiments, the circulating ketone body measured can be D-β-hydroxybutyrate; acetoacetate; or both. Measured amounts of any of these species at these off-peak times are then optionally adjusted to reflect the predicted level at the predicted peak time. In one embodiment, the predicted peak time is at about two hours. Peak circulating blood level and timing can vary depending on factors known to those of skill in the art, including individual digestive rates, co-ingestion or pre- or post-ingestion of foods, beverages, and so on, as known to those of skill in the art.

In one embodiment, the peak blood level reached of species D-β-hydroxybutyrate is between about 0.05 millimolar (mM) to about 50 mM. Another way to determine whether blood levels of D-β-hydroxybutyrate are raised to about 0.05 to about 50 mM in the blood is to determine D-β-hydroxybutyrate urinary excretion, where a level which corresponds to the foregoing blood levels is in a range of about 5 milligrams per deciliter (mg/dL) to about 160 mg/dL. In other embodiments, the peak blood level D-β-hydroxybutyrate is raised to about 0.15 to about 2 mM, to about 0.15 to about 0.3 mM. In other embodiments, the peak blood level of D-β-hydroxybutyrate is raised to at least about 0.05 mM, to at least about 0.1 mM, to at least about 0.15 mM, to at least about 0.2 mM, to at least about 0.5 mM, to at least about 1 mM, to at least about 2 mM, to at least about 2.5 mM, to at least about 3 mM, to at least about 4 mM, to at least about 5 mM, to at least about 10 mM, to at least about 20 mM, to at least about 30 mM, to at least about 40 mM, to at least about 50 mM. In another embodiment, the circulating concentration of at least one type of ketone body are levels of about 0.1 mM; in the range of 0.1 to 50 mM, in the range of 0.2-20 mM, in the range of 0.3-5 mM, and in the range of 0.5-2 mM.

Effective amounts of dosages of compounds for the inventive compositions, i.e., compounds capable of elevating ketone body concentrations in an effective amount, in some embodiments, the first composition, will be apparent to those skilled in the art, and can be conveniently determined by determining the amount of ketone body generated in the blood. Where the compound capable of elevating ketone body levels is monoacetoacetin, the monoacetoacetin dose, in one embodiment, will be in the range of 0.05 g/kg/day to 10 g/kg/day of monoacetoacetin. In another embodiment, the dose will be in the range of 0.25 g/kg/day to 5 g/kg/day of monoacetoacetin. In another embodiment, the dose will be in the range of 0.5 g/kg/day to 2 g/kg/day of monoacetoacetin. In other embodiments, the dose will be in a range of about 0.1 g/kg/day to about 2 g/kg/day. In other embodiments, the dose of monoacetoacetin is at least about 0.05 g/kg/day, at least about 0.1 g/kg/day, at least about 0.15 g/kg/day, at least about 0.2 g/kg/day, at least about 0.5 g/kg/day, at least about 1 g/kg/day, at least about 1.5 g/kg/day, at least about 2 g/kg/day, at least about 2.5 g/kg/day, at least about 3 g/kg/day, at least about 4 g/kg/day, at least about 5 g/kg/day, at least about 10 g/kg/day, at least about 15 g/kg/day, at least about 20 g/kg/day, at least about 30 g/kg/day, at least about 40 g/kg/day, and at least about 50 g/kg/day.

Convenient unit dosage containers and/or formulations include tablets, capsules, lozenges, troches, hard candies, nutritional bars, nutritional drinks, metered sprays, creams, and suppositories, among others. The compositions may be combined with a pharmaceutically acceptable excipient such as gelatin, oil, and/or other pharmaceutically active agent(s). For example, the compositions may be advantageously combined and/or used in combination with other therapeutic or prophylactic agents, different from the subject compounds. In many instances, administration in conjunction with the subject compositions enhances the efficacy of such agents. For example, the compounds may be advantageously used in conjunction with antioxidants, compounds that enhance the efficiency of glucose utilization, and mixtures thereof, (see e.g. Goodman et al. 1996).

In a preferred embodiment the human subject is intravenously infused with an inventive composition, such as, for example, monoacetoacetin, directly, to a level required to treat and prevent the occurrence of diseases associated with hypometabolism. Preparation of intravenous solutions is well known to those skilled in the art.

Additional metabolic adjuvants include energy enhancing compounds, such as Coenzyme CoQ-10, creatine, L-carnitine, n-acetyl-carnitine, L-carnitine derivatives, and mixtures thereof. These compounds enhance energy production by a variety of means. Carnitine will increase the metabolism of fatty acids. CoQ10 serves as an electron carrier during electron transport within the mitochondria. Accordingly, addition of such compounds to an inventive composition such as monoacetoacetin will increase metabolic efficiency especially in individuals who may be nutritionally deprived.

Administration of inventive compositions, such as monoacetoacetin, result in elevated ketone body levels even if large amounts of carbohydrate are consumed at the same time (for overview see (Odle 1997); see also U.S. Patent Provisional Patent Application Ser. No. 60/323,995, "Drug Targets for Alzheimer's Disease and Other Diseases Associated with Decreased Neuronal Metabolism," filed Sep. 21, 2001). The advantages of the Applicant's approach are clear, since careful monitoring of what is eaten is not required and compliance is much simpler.

In one embodiment, the invention comprises the co administration of an inventive composition such as those containing monoacetoacetin and L-carnitine or a derivative of L-carnitine. Thus in the present invention inventive compositions containing, for example, monoacetoacetin, are combined with L-carnitine at doses required to increase the utilization of said monoacetoacetin. The dosage of L-carnitine and monoacetoacetin will vary according to the condition of the host, method of delivery, and other factors known to those skilled in the art, and will be of sufficient quantity to raise blood ketone levels to a degree required to treat and prevent diseases of hypometabolism as defined herein. Derivatives of L-carnitine which may be used in the present invention include but are not limited to decanoylcarnitine, hexanoylcarnitine, caproylcarnitine, lauroylcarnitine, octanoylcarnitine, stearoylcarnitine, myristoylcarnitine, acetyl-L-carnitine, O-Acetyl-L-carnitine, and palmitoyl-L-carnitine. In one embodiment, the invention provides a formulation comprising a mixture of monoacetoacetin and carnitine to provide elevated blood ketone levels. The nature of such formulations will depend on the duration and route of administration. Such formulations will be in the range of 0.05 g/kg/day to 10 g/kg/day of monoacetoacetin and 0.05 mg/kg/day to 10 mg/kg/day of carnitine or its derivatives. In one embodiment, a monoacetoacetin dose will be in the range of 0.05 g/kg/day to 10 g/kg/day of monoacetoacetin. More preferably, the dose will be in the range of 0.25 g/kg/day to 5 g/kg/day of monoacetoacetin. More preferably, the dose will be in the range of 0.5 g/kg/day to 2 g/kg/day of monoacetoacetin. In some embodiments, a carnitine or carnitine derivative dose will be in the range of 0.05 g/kg/day to 10 g/kg/day. More preferably, the carnitine or carnitine derivative dose will be in the range of 0.1 g/kg/day to 5 g/kg/day. More preferably, the carnitine or carnitine derivative dose will be in the range of 0.5 g/kg/day to 1 g/kg/day. Variations will necessarily occur depending on the formulation and/or host, for example.

In one embodiment, the composition comprises a formulation comprising a range of 1-500 g of monoacetoacetin combined with 1-2000 mg of carnitine. Amounts of monoacetoacetin can be at least about 1 g, at least about 10 g, at least about 50 g, at least about 100 g, at least about 150 g, at least about 200 g, at least about 250 g, at least about 300 g, at least about 400 g. Amounts of carnitine can be at least about 1 mg, at least about 50 mg, at least about 100 mg, at least about 250 mg, at least about 500 mg, at least about 1000 mg, at least about 1250 mg, or at least about 1500 mg. An even more preferred formulation comprises 50 g monoacetoacetin emulsified with 50 g of mono- and di-glycerides combined with 500 mg of L-carnitine. Such a formulation is well tolerated and induces hyperketonemia for 3-4 hours in healthy human subjects.

In another embodiment, the invention further comprises determination of the patient's genotype or particular alleles. This method can further comprise selecting patients for treatment based on the results of the determination. In one embodiment, the patient's alleles for apolipoprotein E gene are determined. In some examples, the inventor teaches that non-E4 carriers performed better than those with the E4 allele when elevated ketone body levels were induced with compositions of the present invention including monoacetoacetin. In addition, those with the E4 allele had higher fasting ketone body levels and the levels continued to rise at the two-hour time interval. Therefore, E4 carriers may require higher ketone levels or agents that increase the ability to use the ketone bodies that are present. Accordingly, in one embodiment for those with the E4 allele dosages to administer include a dose of monoacetoacetin combined with agents that increase the utilization of fats, monoacetoacetin or ketone bodies. Examples of agents that increase utilization of fatty acids may be selected from a group comprising of, but not limited to, non-steroidal anti-inflammatory agents (NSAIDs), statin drugs (such as Lipitor® and Zocor®) and fibrates (as discussed elsewhere herein).

In another embodiment of the present invention, further benefit can be derived from formulation of a pharmaceutical composition comprising a compound capable of elevating ketone body concentrations in a patient, such as monoacetoacetin, and an additional therapeutic agent, such as, for example, anti-Alzheimer's agents, anti-diabetic agents, agents capable of increasing utilization of lipids, anti-atherosclerotic agents, anti-hypertensive agents, anti-inflammatory agents, anti-obesity agents, and combinations thereof. In one embodiment, the other therapeutic agents are ones used in the treatment of Alzheimer's disease, Parkinson's disease, traumatic brain injury, Huntington's Disease, or epilepsy.

In some methods of the invention, both the ketogenic compounds of the present invention and the therapeutic agent(s), or the first composition and the second composition, are administered to mammals (e.g., humans, male or female) using respective conventional methods. Administration of each composition referenced herein can be in a dosage form and schedule in accordance with current protocols, recommendations, or schedules known in the art for that composition and/or compound. In this embodiment, the administration of the ketogenic compounds of the present invention and the therapeutic agent(s) will be in accordance with protocols and/or dosing regimes specific to each, but will occur in a manner that administration of ketogenic compounds of the present invention and a therapeutic agent(s) are at least partially overlapping in a specific mammal during a specific treatment regimen. In one embodiment, the administration of the ketogenic compounds of the present invention and the therapeutic agent(s) is substantially overlapping during a treatment regimen. In one embodiment, the treatment regimens for the first and second compositions will overlap sufficiently in order for the beneficial effects as noted herein to occur.

The ketogenic compounds of the present invention and the therapeutic agent(s) may also be employed together in the same oral dosage form or in separate oral dosage forms taken at the same time. The compositions described above may be administered in single or multiple doses of one to four times daily. It may be advisable to start a patient on a low dose combination and work up gradually to a high dose combination.

EXAMPLES

The following examples are provided for illustrative purposes only and are not intended to limit the scope of the invention.

Example 1

Mouse Pharmacokinetic (PK) Study

The inventor examined the blood levels of ketone bodies after oral (po) and intraperitoneal (ip) dosing of monoacetoacetin at different time points in the mouse.

ICR male mice 6 to 7 weeks old were used. Each mouse weighed between 20-30 grams. Animals were housed 3 per cage and were acclimated for at least 3 days prior to dosing. Mice were given either a single po dose (ranging from 2.5, 5 and 10 ml/kg) of compound, or a single ip dose (1 g/kg). Animals were anesthetized for blood collection at the times 15, 30, 60 and 180 minutes. Whole blood (~0.4 mls) was collected via cardiac puncture and collected into sodium heparin anticoagulant (Na Heparin, 1:9 ratio). Blood was centrifuged for 8 minutes at 13,000 rpm to isolate plasma. The plasma was transferred into pre-labeled, color-coded eppendorf tubes and frozen at −70° C. Animals were observed for signs of toxicity and clinical observations recorded. Plasma levels of beta-hydroxybutyrate (BHB) were determined using a beta-hydroxybutyrate detection kit following manufacturer's directions (StanBio Inc.).

Monoacetoacetin (also referenced herein as AC-0523) resulted in significant increases in circulating BHB levels in as early as 15 minutes (see FIG. 1A-D).

Example 2

Use of an Monoacetoacetin to Elevate Serum Ketone Levels in a Rat Model

Sprague-Dawley rats are fed a standard commercial rat chow. After 15 days of acclimation, two groups of rats are fed an experimental diet containing 1-5 g/kg/day of an monoacetoacetin. A control group is kept on a standard isocaloric chow.

The weight of each rat is measured daily. Urine samples are collected daily and analyzed for 3-hydroxybutyrate by enzymatic assay. After 5 days on the experimental diet, the rats are euthanized, and a blood sample was collected and analyzed for 3-hydroxybutyrate, acetoacetate and acetone by standard enzymatic techniques.

The concentration of ketone bodies in the rat blood plasma collected at time of euthanasia is measured by enzymatic methods. The control group is expected to show normal concentrations of 3-hydroxybutyrate and acetoacetate, approximately, 0.02-0.07 mM. Rats fed the monoacetoacetin are expected to have elevated 3-hydroxybutyrate, acetoacetate and acetone concentrations. These results show that rats fed monoacetoacetin had increased levels of ketone bodies in their blood.

The concentration of 3-hydroxybutyrate in the urine of rats fed monoacetoacetin is determined by GC-MS to be approximately 1-10 mM, respectively. 3-Hydroxybutyrate is undetectable in the urine of the control rats. These results show that an oral dose of monoacetoacetin elevates the ketone body concentration in the blood and in the urine.

Example 3

Neuroprotective Effects in MPTP Lesioned Mice

To test the possible therapeutic potential of AC-0523 a small pilot experiment was performed examining the potential neuroprotective effects of AC-0523 in a mouse model of Parkinson's disease (PD). 1-methyl-4-phenyl-1,2,3,6-tetrahydropyridine (MPTP), blocks complex I (NADH-ubiquinone oxidoreductase) of the mitochondrial electron transport chain, and causes typical symptoms of (PD) and the loss of dopaminergic neurons.

Systemic injection of MPTP, upon conversion to MPP+, produces a loss of nigrostriatal dopamine (DA) nerve terminals and eventual death of striatal dopaminergic neurons. This neuropathology mimics conditions in the dopamine denervated striatum of human PD patients, and produces hyperactivity and postural instability. Assays for tyrosine hydroxylase (TH), the enzyme responsible for catalyzing the production of dopamine, and quantification of TH-containing cells in the SNc are performed to measure the extent of striatal dopaminergic neurodegeneration. Tyrosine hydroxylase is reliable marker of dopaminergic nerve fibers, and has been found to decrease in both human PD patients and animal models of the disease.

A parallel group design was used. After acclimation in the facility, subjects were tested on the Rotarod and activity tasks. On the second day of test treatment, all subjects began an 8 day ip administration of MPTP or saline. Fifteen minutes before MPTP or saline treatment and 2.75 hours after, subjects received either the test compound or saline. On the first and ninth treatment day blood draws were taken for subsequent monitoring of β-hydroxybutyrate. On treatment day 11 all subjects were euthanized and histology was preformed on a small number of test animals.

AC-0523 protected tyrosine hydroxylase (TH) expressing cells from MPTP toxicity. Animals treated with AC-0523 had an average density of TH+ neurons of (111±20) which was comparable to Saline treated animals (111±11) and higher than animals treated with MPTP (78±12) (see table below).

| TH+ neuron density in substantia nigra | | | |
|---|---|---|---|
| Level | Number | Mean | Std Error |
| AC0523 MPTP | 3 | 111.000 | 20.013 |
| Saline MPTP | 9 | 78.333 | 11.555 |
| Saline Saline | 8 | 111.250 | 12.256 |

Figure 1:
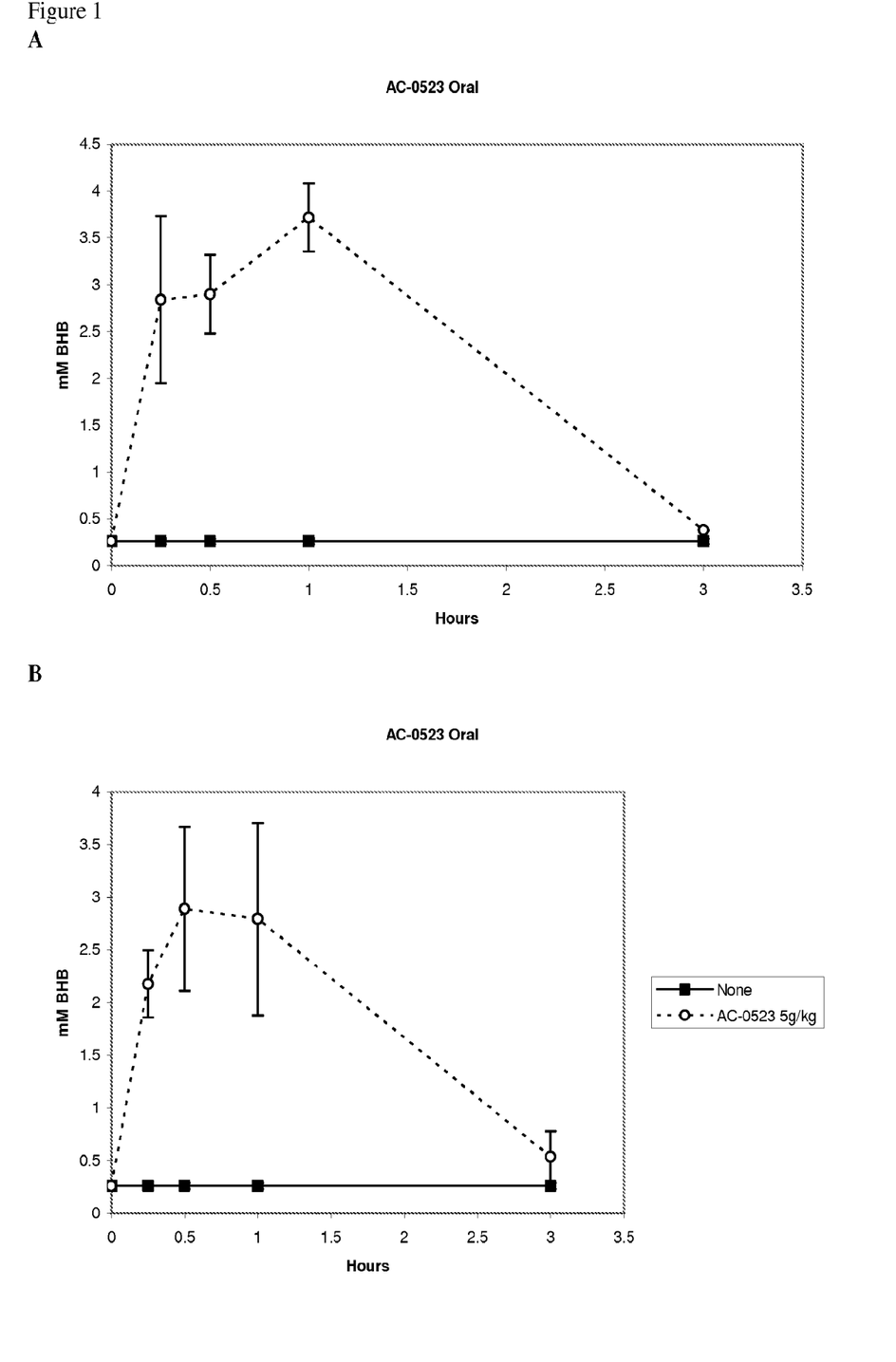
FIGS. 1A through 1D show the blood levels of β-hydroxybutyrate (mM) over time (hour) in mice administered varying amounts of monoacetoacetin.
Figure 2:
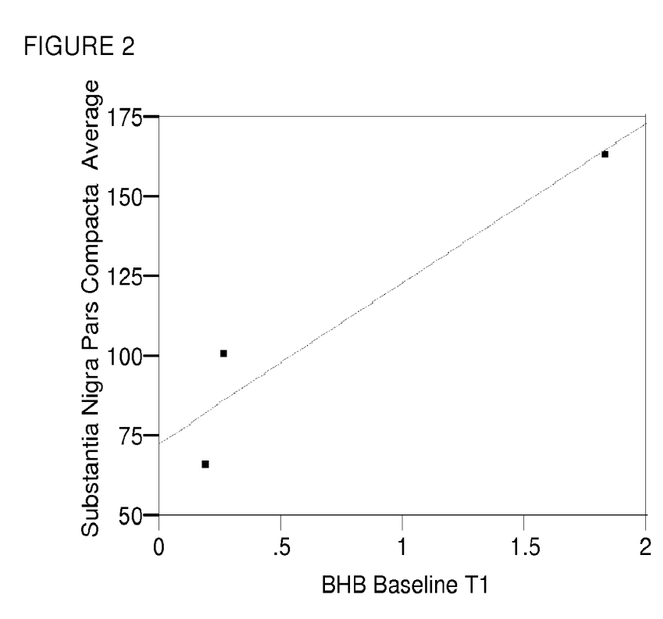
FIG. 2 shows a correlation between animals with higher starting BHB levels and a larger number of TH+ neurons at time of autopsy.

In general, animals with higher starting BHB levels had larger number of TH+ neurons at time of autopsy, again demonstrating that AC-0523 was neuroprotective under these conditions (see correlation at FIG. 2).

MPTP Conclusions

There is support of the neuroprotective role of AC-0523 in MPTP-treated subjects. TH-positive cell counts in the SNc of MPTP-treated mice who were also administered AC-0523 were higher than MPTP-treated mice who received only saline or AC-1202, and comparable to mice who did not receive MPTP. The density of TH in the caudate-putamen was lowest in animals treated with MPTP and saline and highest in subjects who received MPTP and AC0523.

Example 4

To Evaluate the Safety, Tolerability and Effectiveness of Monoacetoacetin in Alzheimer's Disease Monoacetoacetin is administered once a day for ninety days in subjects with mild to moderate, probable Alzheimer's disease. A randomized, double-blind, placebo-controlled, parallel, multi-center design is used. Following a screening period of up to four weeks, subjects will receive either compound 2 or placebo for ninety days followed by a two-week washout period.

Study subjects are 100 outpatients diagnosed as having probable Alzheimer's disease of mild to moderate severity. During the double-blind period of the protocol, 50 subjects receive active medication, and 50 subjects receive placebo.

Monoacetoacetin or matching placebo will be administered once a day for ninety days. Following the end of the ninety-day dosing period, subjects will have a two-week study medication washout period. Each subject is seen five (5) times: at Screening, Baseline, and post-baseline Days 45, 90, and 104. Adverse events, vital signs, weight, physical examinations, 12-lead ECGs, laboratory tests are examined. Primary outcome measures are: Alzheimer's Disease Assessment Scale—Cognitive Subscale (ADAS-Cog), Alzheimer's Disease Cooperative Study—Clinician's Global Impression of Change (ADCS-CGIC) and the Mini-Mental State Examination (MMSE). It is anticipated that subjects treated with monoacetoacetin will show improvement in one or more outcome measures, including ADAS-Cog, ADCS-CGIC or MMSE.

β-Hydroxybutyrate levels are measured pre-dose and 2 hr post-dose on Day 0 (Baseline), Day 45, and Day 90. β-Hydroxybutyrate Cmin levels are also measured at Screening and at the conclusion of the washout period (Day 104). ApoE genotype will be measured on subjects that provide consent. It is anticipated that subjects treated with compound 2 will show elevated serum ketone body levels.

Example 5

Nutritional Drinks and Additional Formulations

A. Ready to Drink Beverage. Ready to Drink Beverages are prepared using the following ingredients: emulsified monoacetoacetin 5-100 g/drink, L-carnitine 250-1000 mg/drink, and a variety of flavorings and other ingredients used to increased palatability, stability, etc.

B. Powdered Beverages. monoacetoacetin may be prepared in a dried form, useful for food bars and powdered beverage preparations. A powdered beverage may be formed from the following components: dried emulsified monoacetoacetin 10-50 g, L-carnitine 250-500 mg, sucrose 8-15 g, maltodextrin 1-5 g, flavorings 0-1 g.

C. Food bar. A food bar would consist of: dried emulsified monoacetoacetin 0.1-50 g, L-carnitine 250-500 mg, glycerin 1-5 g, corn syrup solids 5-25 g, cocoa 2-7 g, coating 15-25 g.

D. Gelatin Capsules. Hard or soft gelatin capsules are prepared using the following ingredients: monoacetoacetin 0.1-1000 mg/capsule, L-carnitine 250-500 mg/capsule, Starch, NF 0-600 mg/capsule; Starch flowable powder 0-600 mg/capsule; Silicone fluid 350 centistokes 0-20 mg/capsule. The ingredients are mixed, passed through a sieve, and filled into capsules.

E. Tablets. Tablets are prepared using the following ingredients: monoacetoacetin 0.1-1000 mg/tablet; L-carnitine 250-500 mg/tablet; Microcrystalline cellulose 20-300 mg/tablet; Starch 0-50 mg/tablet; Magnesium stearate or stearate acid 0-15 mg/tablet; Silicon dioxide, fumed 0-400 mg/tablet; silicon dioxide, colloidal 0-1 mg/tablet, and lactose 0-100 mg/tablet. The ingredients are blended and compressed to form tablets.

F. Suspensions. Suspensions are prepared using the following ingredients: 0.1-1000 mg monoacetoacetin; 250-500 mg L-carnitine; Sodium carboxymethyl cellulose 50-700 mg/5 ml; Sodium benzoate 0-10 mg/5 ml; Purified water 5 ml; and flavor and color agents as needed.

G. Parenteral Solutions. A parenteral composition is prepared by stirring 1.5% by weight of monoacetoacetin and L-carnitine in 10% by volume propylene glycol and water. The solution is made isotonic with sodium chloride and sterilized.

The description of the present invention has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiment described and shown in the figures was chosen and described in order to best explain the principles of the invention, the practical application, and to enable others of ordinary skill in the art to understand the invention for various embodiments with various modifications as are suited to the particular use contemplated.

What is claimed is:

1. A method of treatment for Parkinson's disease, comprising:
   a) selecting a patient having Parkinson's disease;
   b) determining the ApoE status of the patient;
   c) administering to the patient having an absence of ApoE4 a composition comprising an effective amount of monoacetoacetin, or a pharmaceutically acceptable salt thereof, wherein the composition lacks a source of D-β-hydroxybutyric acid or its corresponding salt, in an amount effective to elevate the patient's blood level of ketone bodies.

2. The method of claim 1, wherein the monoacetoacetin is administered at a dose in the range of 0.1 g/kg/day to 10 g/kg/day.

3. The method of claim 1 wherein the patient's blood level of ketone bodies is elevated to 0.2 mM to 20 mM at about two hours post administration.

4. The method of claim 1, wherein the composition further comprises a carbohydrate source.

5. The method of claim 4, wherein the carbohydrate source is glucose.

* * * * *